United States Patent
Yoshioka et al.

(10) Patent No.: US 11,788,206 B2
(45) Date of Patent: Oct. 17, 2023

(54) THREAD COLLECTING DEVICE

(71) Applicant: NATIONAL AGRICULTURE AND FOOD RESEARCH ORGANIZATION, Ibaraki (JP)

(72) Inventors: Taiyo Yoshioka, Ibaraki (JP); Tsunenori Kameda, Ibaraki (JP)

(73) Assignee: NATIONAL AGRICULTURE AND FOOD RESEARCH ORGANIZATION, Ibaraki (JP)

(*) Notice: Subject to any disclaimer, the term of this patent is extended or adjusted under 35 U.S.C. 154(b) by 747 days.

(21) Appl. No.: 16/650,987

(22) PCT Filed: Sep. 27, 2017

(86) PCT No.: PCT/JP2017/034986
§ 371 (c)(1),
(2) Date: Mar. 26, 2020

(87) PCT Pub. No.: WO2019/064382
PCT Pub. Date: Apr. 4, 2019

(65) Prior Publication Data
US 2020/0277710 A1    Sep. 3, 2020

(51) Int. Cl.
*D01B 7/06* (2006.01)
*A01K 67/04* (2006.01)

(52) U.S. Cl.
CPC ............... *D01B 7/06* (2013.01); *A01K 67/04* (2013.01)

(58) Field of Classification Search
None
See application file for complete search history.

(56) References Cited

U.S. PATENT DOCUMENTS 3,994,259 A    11/1976  Sakamura

FOREIGN PATENT DOCUMENTS

| CN | 1389105 A | * | 1/2003 |
| CN | 1596634 A | * | 3/2005 |
| CN | 201025829 Y | | 2/2008 |
| CN | 104663589 A | | 6/2015 |
| CN | 105284747 A | | 2/2016 |
| CN | 206438204 U | | 8/2017 |
| JP | 2011078361 A | | 4/2011 |
| JP | 2014162021 A | | 9/2014 |
| WO | 2012080510 A1 | | 6/2012 |
| WO | 2012165477 A1 | | 12/2012 |

OTHER PUBLICATIONS

Rhainds et al., Bionomics of Bagworms (Lepidoptera: Psychidae). Annual Review of Entomology, 2009. 54:209-226.*
Rajan RK, Tamiolnokuchi, Datta RK. Manual on Mounting and Harvesting Technology. JICA Bivoltine Sericulture Technology development Project, CSR & TI Mysore. Printed at Jawalamukhi Job press 4411. R. K Road, Basavaangdi Bangalore, 1996, 22 pages.*
VWR Collection Catalog 2014-216. p. 79. Downloaded on Dec. 13, 2022 from https://media.vwr.com/interactive/publications/VWR_collection_catalog_2014-2016/files/assets/basic-html/page81.html.*
Kaufmann, Tohko. Observations on the Biology and Behavior of the Evergreen Bagworm Moth, Thyridopteryx ephemeraeformis (Lepidoptera: Psychidae). Annals of the Entomological Society of America, 1968. 61(1): 38-44.*
Sugiura, Shinji. Bagworm Bags as Portable Armour Against Invertebrate Predators. PeerJ, 2016. 4:e1686. 14 pages.*
Kornmilch, Johann-Christoph, "Use of mason bees to pollinate fruit crops: manual for the use of the red mason bee in orchards and allotments", Dec. 31, 2010; retrieved from the internet: URL:http://www.bienenhotel.de/Handbuch_der_Mauerbienenzucht.pdf on Feb. 16, 2021, along with partial English translation (28 pages).
Kornmilch, Johann-Christoph, "Einsatz von Mauerbienen zur Bestäubung von Obstkulturen Handbuch zur Nutzung der Roten Mauerbiene in Obstplantagen und Kleingärten", Dec. 31, 2010; retrieved from the internet: URL:http://www.bienenhotel.de/Handbuch_der_Mauerbienenzucht.pdf on Feb. 16, 2021 (27 pages).
Reddy, Narendra; et al., "Structure and properties of ultrafine silk fibers produced by Theriodopteryx ephemeraeformis", Journal of Material Science, 2010, vol. 45(24), pp. 6617-6622.
EPO, "The extended European search report", issued in connection with European patent application No. 17926995.6, dated Feb. 23, 2021 (5 pages).
Shigeyoshi Osaki, "Animals Teach Science On Natural Fibers: . . .", Journal of the Society of Fiber Science and Technology, vol. 58, No. 3, pp. 74-78, 2002.
Yoshihiko Kuwana, et al., "High-Toughness Silk Produced By a Transgenic Silkworm . . .", PLOS ONE, vol. 9, No. 8, pp. 1-11, 2014.
J.M. Gosline, et al., "The Mechanical Design of Spider Silks: From Fibroin . . .", The Journal of Experimental Biology 202, pp. 3295-3303, 1999.
International Search Report for Corresponding International Application No. PCT/JP2017/034986 (3 Pages) (dated Oct. 31, 2017).
Office Action for Corresponding European Patent Application No. 17926995.6, dated Nov. 3, 2022, 5 pages.

* cited by examiner

*Primary Examiner* — Allison M Fox
*Assistant Examiner* — Kimberly A Aron
(74) *Attorney, Agent, or Firm* — Lucas & Mercanti, LLP

(57) ABSTRACT

A thread collecting method for easily and simply collecting a bagworm-derived pure silk thread from a bagworm with a small number of processes and a thread collecting device for implementing the thread collecting method are developed and provided. A device that collects a silk thread from a bagworm is provided, the device including: a container that accommodates the bagworm; and an in-and-out hole through which the bagworm is put in and taken out of the container. A width of a maximum short axis cross section of an inner space of the container is in a range from 1.2 times or more to less than 3.1 times relative to a maximum body width of the bagworm being accommodated.

12 Claims, 7 Drawing Sheets

A

B

C

THREAD COLLECTING DEVICE

CROSS-REFERENCE TO RELATED APPLICATIONS

This application is a 371 of PCT/JP2017/034986, filed Sep. 27, 2017.

TECHNICAL FIELD

The present invention relates to a device that collects a silk thread(s) derived from a larva of a moth belonging to the family Psychidae, namely, bagworm, (hereinafter, often referred to as "thread collecting device") and also to a method of collecting a bagworm-derived silk thread with high-purity by using the thread collecting device.

BACKGROUND ART

Threads constituting insect cocoons and hairs of mammals have been used as animal fibers for clothes and the like since long time ago. Especially silk threads from a silk moth (*Bombyx mori*) larva, namely a silkworm, which are herein often referred to as "silkworm silk threads", have excellent properties for absorption and desorption of moisture, moisture retention, and heat retention, and also have a unique gloss and smooth texture. Therefore, the silkworm silk threads are valuable and expensive natural materials even today.

However, there exist animal fibers in nature having properties comparable or superior to those of silkworm silk threads. Recently, for utilizing animal fibers having such excellent properties as novel natural materials, exploration thereof and research thereon are ongoing.

Threads derived from spiders (herein often referred to as "spider thread") is one of such materials of interest. Spider threads have flexibility and elasticity and have an elastic force up to 5 to 6 times higher than that of polystyrene, and are thus expected as a medical material for surgical suture and the like, and as a special material for emergency ropes, protective clothes, or the like (Non-Patent Literatures 1 and 2). However, mass-production of spider threads is not possible because mass rearing of spiders and collecting a large amount of threads from spiders are difficult. Another problem is that the production cost is high. Currently, an attempt to overcome these problems is ongoing by using gene recombination technology to produce spider threads in silkworms or *Escherichia coli* (Patent Literature 1 and Non-Patent Literature 2). However, the silkworm or *Escherichia coli* used for spider thread production are recombinants and are thus allowed to be reared or cultured only in facilities having defined equipment, which disadvantageously involves a large maintenance or management burden. Additionally, spider thread proteins expressed in *Escherichia coli* are in a liquid state and are needed to be converted to fibers, which also disadvantageously increases the number of processes. Furthermore, another disadvantage is that currently spider threads spun by the recombinant silkworms are merely comprised in silkworm silk threads at several percentages and cannot be obtained as 100% spider threads which allow 100% of the properties of spider threads to be utilized.

There exist insects called bagworms (also known as "basket worms"). The larvae of moths belonging to the family Psychidae in the order Lepidoptera are collectively referred to as bagworms and are known to spend the whole larval stages living with spindle-shaped or cylinder-shaped nests (bag nests) made of pieces of leaves and twigs assembled by threads (FIG. 1A), during which the larvae usually hide themselves inside the nests and move with the nests even for eating. Bagworms are also insects familiar to people from long time ago, and a bagworm with its nest hanging from a branch of a bare tree in winter time is a typical winter scene.

The bagworm-derived threads (herein often referred to as "bagworm silk threads") have mechanical properties superior to those of silkworm silk threads and spider threads. For example, bagworm silk threads from *Eumeta minuscula* have an elastic modulus up to 3.5 times of that of silkworm silk threads and 2.5 times of that of spider threads of *Nephila clavata*, and have a very high strength (Non-Patent Literatures 1 and 3). Additionally, a monofiber of bagworm silk threads has a cross-sectional area only about one-seventh of that of a monofiber of silkworm silk threads, which allows production of fine, thin and light fabrics with a smooth texture. Moreover, bagworm silk threads have a gloss and a shiny appearance comparable or superior to those of silkworm silk threads.

Bagworms are more advantageous than silkworms also in terms of rearing. For example, since silkworms feed on only raw leaves of mulberry (species belonging to the genus *Morus*, including, for example, *M. bombycis*, *M. alba*, and *M. lhou*) in principle, the region for rearing and season for rearing depend on the supply area of mulberry leaves and the season of mulberry leaf development. In contrast, bagworms are euryphagous, the specificity for food leaves is low, and many species of bagworms can feed on leaves of trees of various species. Accordingly, food leaves for bagworms are easily obtainable and bagworms can be raised in any region. Also, bagworms of some species can feed on leaves of evergreen trees. Thus, differently from mulberries, which are deciduous trees, it is possible to supply food leaves all year round. Moreover, bagworms are smaller in size than silkworms and require a rearing space equal to or less than that required for rearing silkworms, which makes mass rearing easy. Thus, the cost for rearing can significantly be reduced compared with that for rearing silkworms.

Also, bagworms are more advantageous than silkworms in terms of productivity. For example, silkworms spin a large amount of threads only during cocooning and all larvae perform cocooning in the same period. Thus, a disadvantage of silkworms is that thread collection periods overlap and labor periods concentrate thereon. In contrast, bagworms repeatedly spin silk threads for nest building or migration throughout larval stages. Thus, bagworms have an advantage in that labor periods can be dispersed by artificially adjusting the thread collection periods. Additionally, bagworm silk threads can be directly collected from wild-type bagworms, and thus it is not required to generate or maintain recombinants as is required in the case of production of spider threads.

As described above, bagworm silk threads have properties superior to conventional animal fibers and also have many advantages for their production, and thus can be a very promising novel natural material.

However, several major problems have to be solved for the practical application of bagworm silk threads. One of them is the problem derived from the characteristic of the nest, which is the source of bagworm silk threads. Pieces of leaves and twigs and the like are inevitably attached on the surface of bagworm nests, and these contaminants have to be completely removed for commercialization of bagworm silk threads. However, the removing work requires enormous labor and cost, thus resulting in increased production cost.

Additionally, complete removal of the contaminants is difficult with existing technologies, which leads to low quality of final products due to contamination with a small amount of small pieces of leaves as well as light-brown staining of silk threads with pigments from the contaminants and so on.

Accordingly, it has been required to develop a method for easily and simply producing pure bagworm silk threads comprising no contaminants, for practical application of bagworm silk threads as a novel material of biological origin.

CITATION LIST

Patent Literature

Patent Literature 1: International Publication No. WO2012/165477

Non Patent Literature

Non Patent Literature 1: OSAKI Shigeyoshi, 2002, Journal of Fiber Science and Technology (Sen'i Gakkaishi) (Sen'i To Kogyo), 58: 74-78

Non Patent Literature 2: Kuwana Y, et al., 2014, PLoS One, DOI: 10.1371/journal.pone.0105325

Non Patent Literature 3: Gosline J. M. et al., 1999, 202, 3295-3303

SUMMARY OF INVENTION

Technical Problem

The present invention provides and develops a thread collecting method for easily and simply collecting a pure bagworm silk thread from a bagworm with a small number of processes and a thread collecting device for performing the thread collecting method.

Solution to Problem

In a process of making a variety of studies to solve the above problems, the present inventors have found a fact that when a bagworm is placed in a tube with a predetermined inner diameter, the bagworm also spins a thread even inside the tube and the spun silk thread forms into a thread ball (herein, often referred to as "silk thread mass"). The bagworm usually spins a thread for a foothold in a zigzag pattern as shown in FIG. 1C so as not to fall off a branch or the like (arrowhead) and moves while catching the thread with claws (arrows). The bagworm continuously spins a thread for a foothold even in the tube but the thread does not stick to a wall surface in the tube with the predetermined diameter, which possibly results in the formation of the silk thread mass. Such a silk thread mass consists of a pure bagworm silk thread containing none of impurities such as leaf disc and twigs and, further, a considerable amount of the silk thread mass can be obtained. Moreover, the silk thread mass does not stick to a tube inner wall and thus can be easily collected by inverting the tube without the necessity of a separation process or the like. The present invention, which is based on the above new findings, provides the following.

(1) A device that collects a silk thread(s) from a bagworm(s), the device comprising:
a container that accommodates the bagworm; and
an in-and-out hole through which the bagworm is put in and taken out of the container, wherein
a width of a maximum short axis cross section of an inner space of the container is in a range from 1.2 times or more to less than 3.1 times relative to a maximum body width of the bagworm being accommodated.

(2) The device according to (1), wherein
the container has a discharge hole at a bottommost portion, and
the discharge hole has a minimum width longer than a maximum width of excrement of the bagworm being accommodated and a maximum width shorter than a maximum width of a head of the bagworm being accommodated.

(3) The device according to (1) or (2), wherein a long axis of the inner space of the container has an inclination of 60 degrees to 90 degrees relative to a horizontal plane.

(4) The device according to any one of (1) to (3), wherein a shape of the inner space of the container is a tubular shape, a spherical shape, an oval-spherical shape, or a combination thereof.

(5) The device according to any one of (1) to (4), wherein a shape of a short axis cross section of the inner space of the container is a circle, an oval, a polygon, or a combination thereof.

(6) The device according to any one of (1) to (5), wherein an inner wall of the container has a smooth surface.

(7) The device according to any one of (1) to (6), wherein a material of an inside of the container includes an artificial material.

(8) The device according to any one of (1) to (7), wherein the container includes an encapsulating unit configured to encapsulate the bagworm.

(9) A method of collecting a silk thread(s) from a bagworm(s), the method comprising:
accommodating the live bagworm having no nest in the container of the device according to any one of (1) to (8);
spinning by the bagworm in the container; and
collecting the silk thread from the container.

(10) The method according to (9) depending from (8), further comprising:
encapsulating the bagworm in the container after the accommodating and before the spinning; and
canceling the encapsulating after the spinning and before the collecting.

(11) The method according to (9) or (10), wherein the bagworm is in a last instar.

(12) A producing method of producing a silk thread mass of a bagworm, the method comprising:
accommodating the live bagworm having no nest in the container of the device according to any one of (1) to (8);
spinning a silk thread(s) by the bagworm in the container to produce the silk thread mass; and
collecting the silk thread mass from the container.

(13) The producing method according to (12), further comprising:
encapsulating the bagworm in the container after the accommodating and before the spinning; and
canceling the encapsulating after the spinning and before the collecting.

(14) The producing method according to (12) or (13), wherein the bagworm is in a last instar.

Advantageous Effects of Invention

The thread collecting device according to the present invention allows for implementing the thread collecting method according to the present invention.

The thread collecting method according to the present invention allows for easily and simply collecting a pure bagworm-derived silk from a bagworm thread with a small number of processes. In particular, the thread collecting method according to the present invention allows for collecting a silk thread(s) spun in the device in the form of a silk thread mass.

BRIEF DESCRIPTION OF DRAWINGS

FIG. 4A is an example where bagworms are accommodated in the thread collecting device according to the present invention. FIG. 4B shows that the bagworm forms a silk thread mass while spinning a thread inside the container. FIG. 4C shows that the silk thread mass and the bagworm collected from the container. In the figures, each arrow points to the silk thread mass.

FIGS. 5A and 5B each show a result of verification with a container with a discharge hole and FIGS. 5C and 5D each show a result of verification with a comparative container without a discharge hole. FIGS. 5A and 5C each show a state of the silk thread mass in the container and FIGS. 5B and 5D each show the silk thread mass collected from the container.

FIG. 6A is a result of using a container with an inner space having a 9-mm-wide maximum short axis cross section for a bagworm with a maximum body width of 7 mm and FIG. 6B is a result of using a container with an inner space having a 120-mm-wide maximum short axis cross section for a bagworm with a maximum body width of 7 mm. An arrow shown in FIG. 6A points to the silk thread mass formed in the container.

DESCRIPTION OF EMBODIMENTS

1. Thread Collecting Device 1-1. Overview

Figure 1:
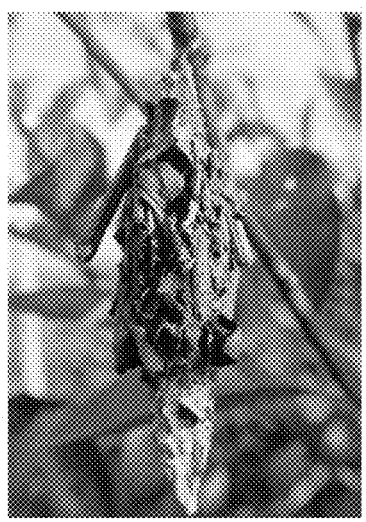
FIG. 1A is an external view of a nest of a bagworm of *Eumeta japonica* (*Eumeta japonica* bagworm).
FIG. 1B is a view showing an inside of a nest halved by longitudinally cutting the nest of the *Eumeta japonica* bagworm, in which an insect in a middle is a larva of *Eumeta japonica*, namely, *Eumeta japonica* bagworm.
FIG. 1C is a view showing a spinning action of the *Eumeta japonica* bagworm during movement, in which it is found that the bagworm advances while spinning a silk thread (arrowhead) and catches the spun silk thread with claws (arrows).
Figure 1:
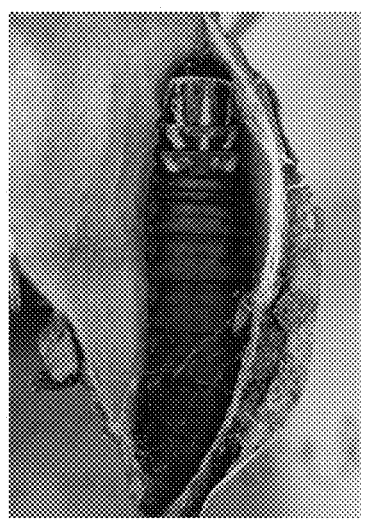
Figure 1:
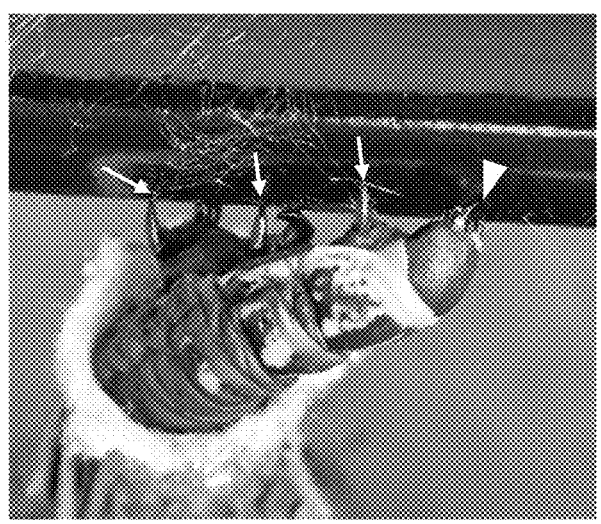

A first aspect of the present invention is a device that collects a silk thread(s) from a bagworm(s) (thread collecting device). The thread collecting device according to the present invention allows for simply and easily collecting an impurity-free pure bagworm silk thread from a bagworm.

1-2. Definition

The term "bagworm" collectively refers to a moth larva belonging to the family Psychidae in the order Lepidoptera, as described above. Moths belonging to the family Psychidae are distributed worldwide and larvae (bagworms) of any species of the moths spend the whole larval stages living in nests covered with natural materials, such as pieces of leaves and twigs, which are assembled by silk threads spun by the larvae themselves. The nests are spindle-shaped, cylinder-shaped, or cone-shaped bag-like nests that can accommodate the whole body of a bagworm. Bagworms usually hide themselves inside the nests and always carry the nests even during eating and migration, and in principle, even pupate inside the nests.

The species, instar, and gender of bagworms used herein are not limited, provided that the bagworms are larvae of a moth species belonging to the family Psychidae and that the species makes a nest as described above. For example, the family Psychidae includes the genera *Acanthopsyche, Anatolopsyche, Bacotia, Bambalina, Canephora, Chalioides, Dahlica, Diplodoma, Eumeta, Eumasia, Kozhantshikovia, Mahasena, Nipponopsyche, Paranarychia, Proutia, Psyche, Pieroma, Siederia, Striglocyrbasia, Taleporia, Theriodopleryx, Trigonodoma*, etc., and bagworms used herein are a species belonging to any genus. Specific examples of Psychidae species include *Eumeta japonica, Eumeta minuscula*, and *Nipponopsyche fuscescens*. The instar of the larvae may be any instar between the first instar and the last instar. However, large bagworms are preferable for the purpose of obtaining thicker and longer bagworm silk threads. For example, among larvae of the same species, larvae in the last instar are more preferable, and female larvae are more preferable than male larvae because females grow larger than males. Additionally, among the family Psychidae, large species are more preferable. Thus, *Eumeta japonica* and *Eumeta minuscula* are species that are suitable as the bagworms used in the present invention.

The term "silk thread" as used herein refers to a proteinous thread from an insect, which is spun by the insect in larval or adult stage for the purpose of nest building, migration, anchoring, cocooning, prey capture, and the like. When the term "silk thread" is simply recited herein, it means bagworm silk thread, unless specifically noted.

The term "bagworm silk thread" as used herein refers to a bagworm-derived silk thread.

1-3. Configuration

The thread collecting device according to the present invention includes a container and an in-and-out hole. The thread collecting device may further include a holding unit and an encapsulating unit as necessary.

The term "container" herein refers to a case for accommodating a bagworm and has an inner space. Although a single container is sufficient for each thread collecting device, the thread collecting device may comprise a plurality of containers.

The term "accommodating" herein refers to placing a whole of a target, that is, bagworm, in the inner space of the container.

The term "inner space (of the container)" refers to a space provided inside the container to accommodate a bagworm.

Figure 2:
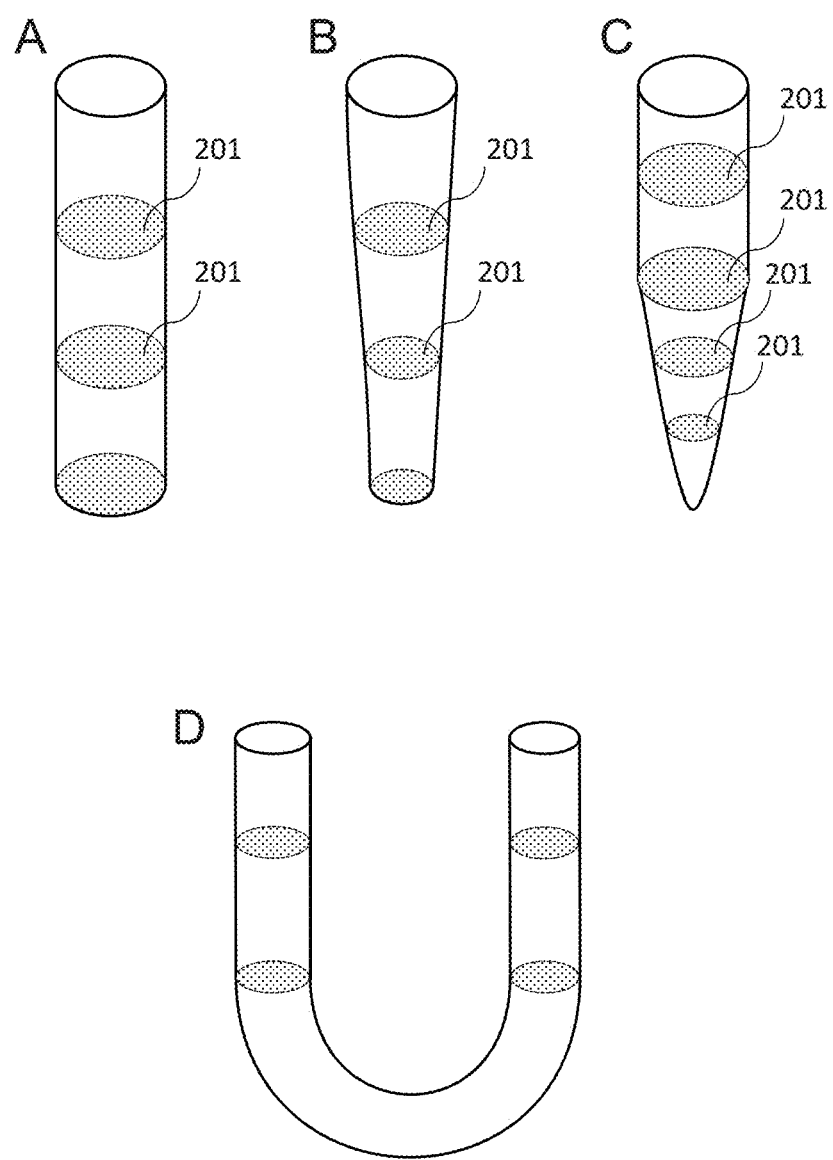
FIGS. 2A to 2D each are a schematic view showing a form example of an inner space of a container of a thread collecting device according to the present invention.

The accommodated bagworm performs a spinning action in this inner space. A shape of the inner space is not limited as long as the shape satisfies later-described conditions and gives no excessive burden, for example, considerably restricting a motion of the bagworm. Examples of the shape include a tubular shape, a spherical shape, an oval-spherical shape, and a combination thereof. The tubular shape or the oval-spherical shape is favorable. The tubular shape may be a parallel tubular shape having an inside with a short axis cross section (201) substantially constant thereacross as shown in FIG. 2A, a conical or pyramidal shape with a short axis cross section (201) gradually tapered toward an end portion as shown in FIG. 2B, or a combination thereof as shown in FIG. 2C. The shape of the short axis cross section of the tubular shape may be any of a circle, an oval, a polygon (including rectangle, hexagon, etc.) or a combination thereof. Moreover, a whole shape of the tubular shape is not limited. For example, the whole shape may be any of a linear shape such as a test tube, a curved shape such as an arc, or a shape including a combination of a line and a curve such as a J-shape or a U-shape shown in FIG. 2D.

The inner space of the container is defined to allow a width of the maximum short axis cross section to fall within a predetermined range.

The term "short axis cross section" herein refers to a cross section including a short axis perpendicular to a long axis of the inner space. The term "maximum short axis cross section" refers to a cross section with the largest area among those of the short axis cross sections of the inner space. For example, in a case where the inner space has an oval-spherical shape (300) such as a spheroid shown in FIG. 3A, a short axis cross section (302) perpendicular to a middle of a long axis (301) corresponds to the maximum short axis cross section. Meanwhile, in a case where the inner space has a spherical shape (303) shown in FIG. 3B, a short axis cross section (302) perpendicular to the middle of long axis (301), that is, a plane including a diameter, corresponds to the maximum short axis cross section. Furthermore, in a case where the inner space has a parallel prismatic shape (304) shown in FIG. 3C, any short axis cross section (302) perpendicular to the long axis (301) corresponds to the maximum short axis cross section.

Figure 3:
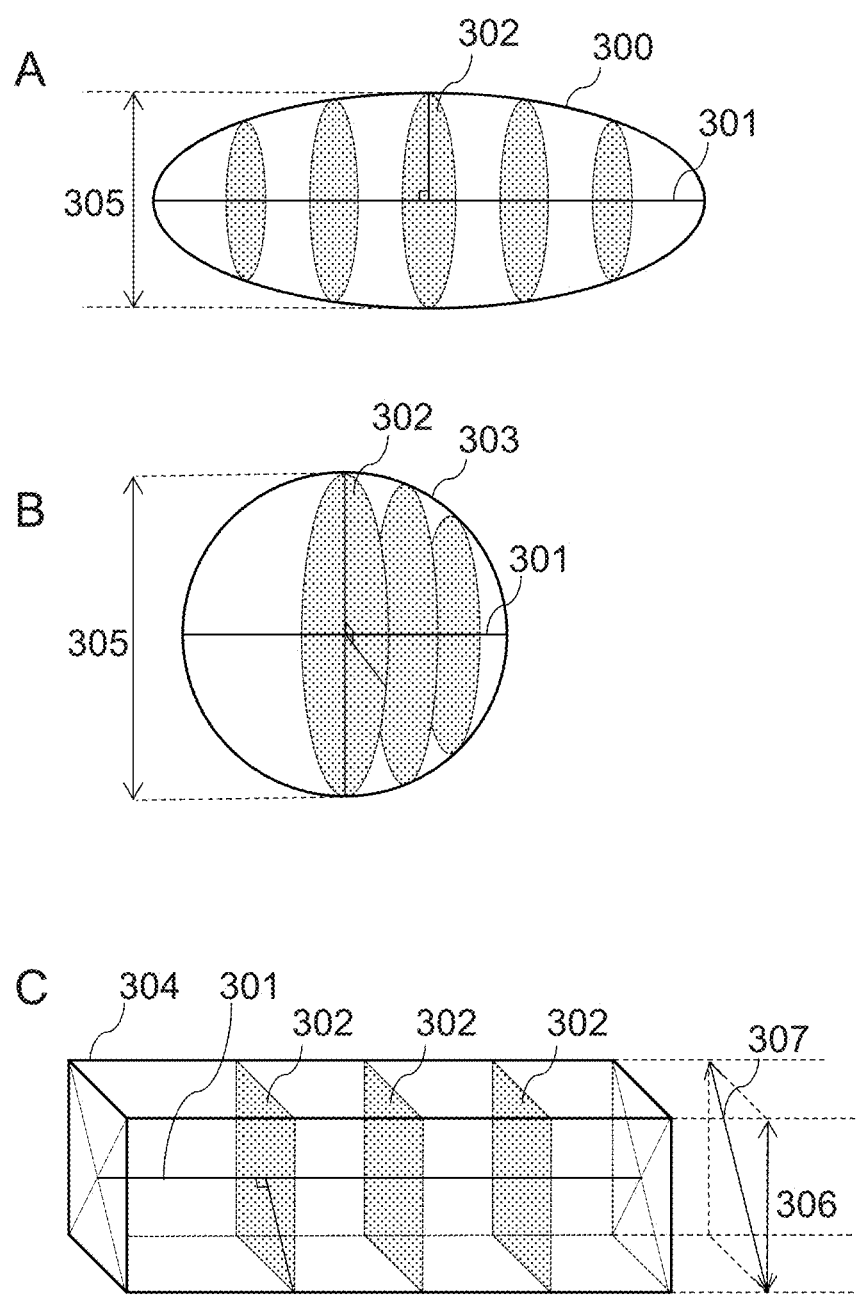
FIGS. 3A to 3C each are a schematic view showing a maximum short axis cross section (302) of the inner space of the container of the thread collecting device according to the present invention and widths (305 to 307) thereof.

The term "width of maximum short axis cross section" herein refers to an entire width of a plane providing the maximum short axis cross section. For example, such a width corresponds to a diameter (305) in the case where the shape of the maximum short axis cross section is a circle as shown in FIG. 3A or FIG. 3B and corresponds to a width corresponding to a side (306) or a diagonal line (307) in the case where the shape of the maximum short axis cross section is a rectangle as shown in FIG. 3C.

The above "within the predetermined range" for the width of the maximum short axis cross section refers to a range from 1.2 times or more to less than 3.1 times, preferably from 1.3 times or more to 2.5 times or less (1.3 times to 2.5 times), relative to a maximum body width of the bagworm being accommodated. The term "body width of the bagworm" refers to a width of the cross section including the short axis perpendicular to the long axis from a head tip portion to a tail tip portion and the term "maximum body width of the bagworm" refers to a maximum body width among body widths of the bagworm. In principle, the maximum body width is a maximum width of an individual bagworm prior to being accommodated, preferably about to be accommodated, in the container. This width, which differs depending on a type, instar (growth stage), sex, and individual difference of each bagworm, may be determined in accordance with the bagworm being used as appropriate. It is typically possible to roughly identify a numerical value of the maximum body width, when the type and instar of the bagworm being used in the thread collecting device according to the present invention are known. For example, a last instar bagworm of *Eumeta japonica* has a maximum body width in a range of 9.0 mm±2.0 mm (7.0 mm to 11.0 mm) on average, preferably in a range of 9.0 mm±1.5 mm (7.5 mm to 10.5 mm) on average. Meanwhile, a last instar bagworm of *Eumeta minuscula* has a maximum body width in a range of 7.0 mm±2.0 mm (5.0 mm to 9.0 mm) on average, preferably a range of 7.0 mm±1.5 mm (5.5 mm to 8.5 mm) on average. Accordingly, in a case of using a last instar bagworm of *Eumeta japonica* in the thread collecting device according to the present invention, the width of the maximum lateral cross section of the inner space of the container may be in a range from 8.4 mm or more to less than 34.1 mm (≈from 7.0 mm×1.2 times or more to less than 11.0 mm×3.1 time) or a range of 9.1 mm to 27.5 mm (≈7.0 mm×1.3 times to 11.0 mm×2.5 times), preferably in a range from 9.0 mm or more to less than 32.6 mm (≈from 7.5 mm×1.2 times or more to less than 10.5 mm×3.1 times) or a range of 9.8 mm to 26.3 mm (≈7.5 mm×1.3 times to 10.5 mm×2.5 times). For example, in a case where the maximum lateral cross section is in the above rectangular shape, a minimum value, that is, a length of a side, may be 9.0 mm or more and a maximum value, that is, a diagonal line, may be 27.5 mm or less.

Meanwhile, a length of the long axis of the inner space is not limited as long as the length is longer than an entire length of the bagworm being accommodated. To allow the bagworm to move in the inner space freely to some extent, a lower limit of the length may be at least 1.5 times, 2.0 times, 2.5 times, 3.0 times, 3.5 times, 4.0 times, 4.5 times, or 5.0 times as large as the entire length of the bagworm. An upper limit of the length is not limited but it is typically sufficient that the upper limit is at most 20 times, 15 times, 14 times, 13 times, 12 times, 11 times, 10 times, 9 times, 8 times, 7 times, or 6 times.

A material constituting the inside of the above container is not limited as long as the material is unlikely to be easily broken or pierced by the bagworm. The material may be a natural material, an artificial material, or a combination thereof. Examples of the natural material include metal (including alloy), mineral (including stone and sand), animal-derived material (including bone, tooth, fang, horn, shell, scale, and horn), and plant-derived material (including wood, bamboo, seed hull, and paper). Examples of the artificial material include synthetic resin (including plastic), ceramics (including vitreous enamel), glass, and carbon fiber. The artificial material is favorable in terms of material cost and production cost.

It is preferable that the above container inner wall, that is, a wall surface of the inside of the container, is a smooth surface. In a case where there are a lot of roughness on the wall surface, the bagworm accommodated in the container is likely to escape by using such a rough portion as a foothold or a spun silk thread is not likely to stick to the wall surface, failing in obtaining a silk thread mass as desired. The smooth surface may be based on the material of the inside of the container itself or may be provided by applying a coating material to a surface of the material of the inside of the container. For example, a material such as metal, glass or plastic may be smoothened itself by a treatment. Meanwhile, even a material difficult to be smoothen, such as a wooden material or fiber, can be provided with smoothness by coating a surface of the material with a coating material such as varnish.

Examples of the container include a test tube and a conical tube.

The term "in-and-out hole" herein refers to a hole allowing a bagworm to be put in and taken out of the inside of the container. A single container may have a single in-and-out hole but may have a plurality of holes. For example, the container may be in the form of a U-shaped tube, both end portions of which are provided with respective in-and-out holes. In a case of providing the plurality of in-and-out holes, a hole for loading a bagworm and a hole for taking out the bagworm may be the same or different. A width of the in-and-out hole has to be larger than the maximum body width of a bagworm being accommodated in the container. The width is typically in a range from 1.2 times or more to less than 3.1 times relative to the maximum body width of the bagworm. A shape of the in-and-out hole, which is not limited as long as being conformable to the shape of the container, is preferably a circle or an oval close to a circle (substantial circle).

The above container may be provided with a discharge hole. The term "discharge hole" of the container refers to a hole for discharging excrement excreted from the bagworm accommodated in the container out of the container. A purpose of the discharge hole is to discharge excrement out of the container in principle. However, a similar effect is achievable with the configuration allows for preventing the larva from again contacting with excrement, and thus the excrement is not necessarily discharged out of the container. Generally, in a case of using a bagworm in an active stage that has an eating behavior in the thread collecting device according to the present invention, the bagworm often excretes excrement in the container. If this excrement is left inside the container, the bagworm starts tangling the excrement as a nest material with a thread, resulting in collection of a silk thread mass contaminated with the excrement and, consequently, failure in obtaining a pure silk thread mass. Accordingly, in the case of using a bagworm in the active stage, it is preferable that the container has the discharge hole.

The discharge hole is located in a bottommost portion of the inside of the container so that excrement excreted in the container is naturally discharged by gravity. The term "bottommost portion" refers to a lowermost level of the inside of the container. In this regard, it is preferable that the inside of the container has a configuration tapered toward the discharge hole. Specifically, it is preferable that the inside of the container has a configuration allowing water put in the container to be fully naturally drained through the discharge hole. A shape of the hole is not limited. The shape of the hole may be any of a circle, an oval, a polygon (including rectangle, hexagon, etc.), or a combination thereof. However, considering that the purpose of the discharge hole is to discharge excrement out of the container and excrement is in a shape close to a sphere as well as easiness to pierce, a circle or an oval close to a circle (substantial circle) is preferable. Regarding a size of the discharge hole, a minimum width of the hole only has to be longer than a maximum width of excrement being excreted from the bagworm accommodated in the container. Meanwhile, a maximum width of the hole is shorter than a maximum width of a head of the bagworm being accommodated in the container to prevent the bagworm from escaping. A width of the discharge hole differs depending on a type, instar (growth stage), sex, and individual difference of each bagworm. Accordingly, the width of the discharge hole may be determined in accordance with the bagworm being used as appropriate. It is typically possible to roughly identify these numerical value, when the type and instar of the bagworm being used in the thread collecting device according to the present invention are known. For example, a last instar bagworm of *Eumeta japonica* has a maximum width of excrement in a range of 3.0 mm±0.5 mm (2.5 mm to 3.5 mm) on average and a head maximum width in a range of 5.5 mm±1.0 mm (4.5 mm to 6.5 mm) on average. Meanwhile, a last instar bagworm of *Eumeta minuscula* has a maximum width of excrement in a range of 2.5 mm±0.5 mm (2.0 mm to 3.0 mm) on average and has a head maximum width of 4.5 mm±1.0 mm (3.5 mm to 5.5 mm) on average. Typically, the width of the discharge hole is at least 1.2 times, 1.3 times, or 1.4 times, preferably 1.5 times, 1.6 times, 1.7 times, 1.8 times, 1.9 times, or 2.0 times, as large as the maximum width of excrement, and at most 0.9 times or 0.8 times, preferably 0.7 times or 0.6 times, as large as the head maximum width.

An external shape of the container is not limited. The external shape may be completely different from that of the inner space or may be conformable to that of the inner space. Examples of the external shape completely different from that of the inner space include a case where the external shape is a quadrangular prism and the inner space is in a cylindrical shape contained therein. Typically, the external shape may be in a shape conformable to that of the inner space.

An angle of the container of the thread collecting device is not limited. For example, the long axis of the inner space of the container may be horizontal or vertical (90 degrees) to a horizontal plane. However, considering an installation space for the thread collecting device, easiness to manage a bagworm, easiness to discharge excrement, or escape of a bagworm from the container, it is preferable that the angle of the container of the thread collecting device is determined to allow the long axis of the inner space to have an inclination of 60 degrees to 90 degrees, 70 degrees to 90 degrees, 80 degrees to 90 degrees, or 85 degrees to 90 degrees relative to the horizontal plane. 90 degrees is the most favorable.

To prevent the accommodated bagworm from getting out through the in-and-out hole and escaping, the container may be configured to encapsulate the bagworm in the inner space as necessary. The term "encapsulate" herein refers to confining the bagworm in the inner space of the container. It is to be noted that the inner space is basically ventilated and thus not sealed for confinement. For encapsulation, the encapsulating unit may be provided on, among holes provided in the container, a hole with a width equal to or larger than the head maximum width of the bagworm. In the container, a hole necessarily larger than the head maximum width of the bagworm is the in-and-out hole in principle, encapsulation is achievable by providing the encapsulating unit on the in-and-out hole.

The term "encapsulating unit" herein refers to a unit that reduces the width of a hole with a width equal to or larger than the head maximum width of the bagworm to be smaller than the head maximum width of the bagworm or closes the hole. A specific example is a lid. A form of the lid is not limited as long as the conditions for the encapsulating unit are satisfied. Lids in a variety of forms, such as a screw cap and a rubber closure, are usable. The lid may have a hole. Alternatively, the encapsulating unit may be a variable unit that can reduce the width of the in-and-out hole to be smaller than the head maximum width of the bagworm as desired.

The term "holding unit" herein refers to a unit that holds the container of the thread collecting device. The holding unit is an optional component for the thread collecting device, since the holding unit is not necessary if the container can be supported by itself and a necessary inclination or the like can be maintained. A shape and a size of the holding unit are not limited. In addition, the holding unit may be configured to hold a plurality of containers. In a case where the container is a test tube, a specific example of the holding unit is a test tube rack or the like.

2. Thread Collecting Method

2-1. Overview

A second aspect of the present invention is a thread collecting method. The thread collecting method according to the present invention is a method of obtaining a pure bagworm silk thread from a bagworm by using the thread collecting device according to the first aspect. The silk thread method according to the present invention allows for simply and easily collecting a bagworm silk thread in a form of a pure silk thread mass.

2-2. Method

The thread collecting method according to the present invention includes an accommodating step, a spinning step, and a collecting step as necessary steps and includes an encapsulating step and a canceling step as optional steps. Each step will be described below.

(1) Accommodating Step

The "accommodating step" is a step of accommodating a bagworm in the container of the thread collecting device according to the first aspect.

A bagworm being used in the present step is a live individual having no nest. A bagworm, which usually acts with a nest, may be taken out of the nest in use. The bagworm being used in the present invention may be an individual in the active stage that has the eating behavior or may be an individual in a dormant stage. It is to be noted that any individual in the dormant stage needs to be placed under conditions for action.

The "conditions for action" herein refer to conditions for a bagworm to do an action accompanied by a routine motion such as moving or eating. Examples of the conditions include atmospheric temperature, atmospheric pressure, moisture, lightness and darkness, and oxygen amount, among which atmospheric temperature is the most important condition for the present invention. Insects are a heterotherm and thus stop action and go into the dormant state with a reduction in atmospheric temperature. Accordingly, a favorable lower limit of atmospheric temperature among the conditions for action according to the present invention is a temperature not causing a bagworm to go into the dormant state. A specific temperature, which differs depending on type, may be 10° C. or higher, preferably 12° C. or higher, more preferably 13° C. or higher, further preferably 14° C. or higher, much further preferably 15° C. or higher, approximately. Meanwhile, an upper limit of atmospheric temperature corresponds to an upper limit of a temperature for a bagworm to live at. Typically, the upper limit may be 40° C. or lower, preferably 35° C. or lower, more preferably 30° C. or lower, further preferably 27° C. or lower, much further preferably 25° C. or lower. The atmospheric pressure, moisture, lightness and darkness, oxygen concentration, etc. may be comparable with, for example, conditions for a flat land in a temperate region. For example, the atmospheric pressure may be around 1 atm., the moisture may be in a range of 30% to 70%, the lightness and darkness may satisfy a lightness condition of 6 hours to 18 hours in 24 hours, and the oxygen concentration in the air may be in a range of 15% to 25%.

Moreover, the bagworm being used in the present invention may be an individual collected in the field or may be an individual in successive generations by artificial rearing. In either case, an individual not in a starvation state is preferable and an individual having been provided with a sufficient amount of food prior to use is more preferable. Unless the individual for thread spinning is in the starvation state, the bagworm, which has been sufficiently fed, keeps on spinning a thread while moving on a rail during a period of 1 hour to 4 days, 3 hours to 3 days, or 6 hours to 2 days under the conditions for action.

The bagworm is accommodated through the in-and-out hole provided in the container of the thread collecting device. The bagworm taken out of the nest is exposed to a stressful environment, so that it is preferable that the bagworm is accommodated promptly after taken out of the nest. At this time, load being applied to the bagworm is eliminated or minimized. The load herein refers to an excessive load except stress, examples of which include a contact load resulting from pinching or rolling the bagworm and a temperature load resulting from exposure to a low temperature or a high temperature.

In principle, one bagworm is put in each container.

(2) Encapsulating Step

The "encapsulating step" is a step of encapsulating the bagworm in the container. The present step is performed after the above accommodating step and before a later-described spinning step. The present step is an optional step and can be performed if the thread collecting device according to the first aspect includes the encapsulating unit. A purpose of the present step is to prevent the bagworm accommodated in the container in the accommodating step from getting out of the container.

The present step is a presupposed step for a later-described canceling step and is usually performed in a pair with the canceling step. However, the encapsulating step may be solely performed.

The encapsulation is achieved by closing the out-and-in hole with the encapsulating unit. The encapsulation may be performed by a method according to a configuration of the encapsulating unit provided. For example, in a case of the encapsulating unit being a screw cap, an opening of the container corresponding to the out-and-in hole may be covered by screwing the screw cap thereinto.

(3) Spinning Step

The "spinning step" is a step of letting the bagworm spin a silk thread(s) in the container. The present step is the most important step for producing a bagworm silk thread according to the present invention. However, it is sufficient that the thread collecting device is placed under the conditions for action and no any other special operation is necessary. When the bagworm is accommodated in the container, the bagworm voluntarily keeps on spinning a thread in the container and the spun bagworm silk thread that naturally forms into a silk thread mass. A time being spent on the present step, that is, a time being spent letting the bagworm spin a thread, is not limited. The present step only has to be performed until the silk thread mass is formed in the container. The present step may be performed for 6 hours or more, 12 hours or more, 18 hours or more, 24 hours or more, 48 hours or more, or 72 hours or more. An upper limit may be a time elapsed before the bagworm stops spinning and typically 168 hours or less, 150 hours or less, 144 hours or less, 120 hours or less, 100 hours or less, or 96 hours or less is sufficient.

(4) Canceling Step

The "canceling step" is a step of canceling the encapsulation. The present step is performed after the above spinning step and before a later-described collecting step. The present step is an optional step that presupposes that the encapsulating step has been performed and can be performed if the thread collecting device according to the first aspect includes the encapsulating unit. A purpose of the present step is to make it easy to collect, from the container, the silk thread mass created from the thread spun by the bagworm in the above spinning step in the container.

The term "canceling" refers to decapsulating. That is, the canceling refers to separating the encapsulating unit from the in-and-out hole according to the present method. For example, in a case where the encapsulating unit is a screw cap, the cap may be removed from the container.

Since the in-and-out hole is opened by the present step, it is possible to easily collect the silk thread mass created in the container in a later-described collecting step.

(5) Collecting Step

The "collecting step" refers to a step of collection from the container. The silk thread is collected through the in-and-out hole in principle. However, the silk thread may be collected through the discharge hole or a hole provided in the encapsulating unit using tweezers or the like. The silk thread produced in the container, which is in the form of a silk thread mass, usually has a size smaller than the width of the in-and-out hole. Thus, in a case of being collected through the in-and-out hole, the silk thread can be easily collected merely by turning the in-and-out hole downward. At this time, tweezers, a scratch stick, or the like may be used if necessary. The bagworm accommodated in the container in the accommodating step may be collected along with the silk thread in the present step. The bagworm may be used again. Accordingly, the bagworm may be continuously accommodated in the container to let the bagworm spin again if necessary. However, the bagworm having been used once in the present method is exhausted as having kept on spinning in a fasting state, so that it is preferable that the bagworm is used after collected once and fed with leaves.

3. Silk Thread Mass Producing Method 3-1. Overview

A third aspect of the present invention is a silk thread mass(es) producing method. The producing method according to the present invention allows for producing a silk thread mass made of a bagworm silk thread(s) by using the thread collecting device according to the first aspect. The producing method according to the present invention allows for simply and easily producing a silk thread mass(es) made of a pure bagworm silk thread.

3-2. Method

The producing method according to the present invention includes the accommodating step, the spinning step, and the collecting step as necessary steps and includes the encapsulating step and the canceling step as optional steps. Details of these steps are conformable to those of the steps of the thread collecting method according to the second aspect. Accordingly, specific descriptions of the steps are omitted.

EXAMPLES

Example 1: Production of Silk Thread Mass by Thread Collecting Device (1)

(Purpose)

A purpose is to verify that use of the thread collecting device according to the present invention allows for easily and simply collecting a silk thread mass made of a pure bagworm silk thread containing no contaminant.

(Method)

Bagworms being used were last instar larvae of *Eumeta japonica* collected in the field in November. Each individual was in a range of 9.0 mm to 10.0 mm in maximum body width and in a range of 30.0 mm to 32.0 mm in entire length.

A 10 mL polypropylene conical tube (manufactured by IWAKI CO., LTD.) was used as the container of the thread collecting device. A maximum short axis cross section of an inner space of this container has a width (inner diameter) of 14.5 mm and a length of 97.0 mm. In this case, a tube opening corresponds to the in-and-out hole of the container. Moreover, a test tube rack was used as the holding unit.

Figure 4:
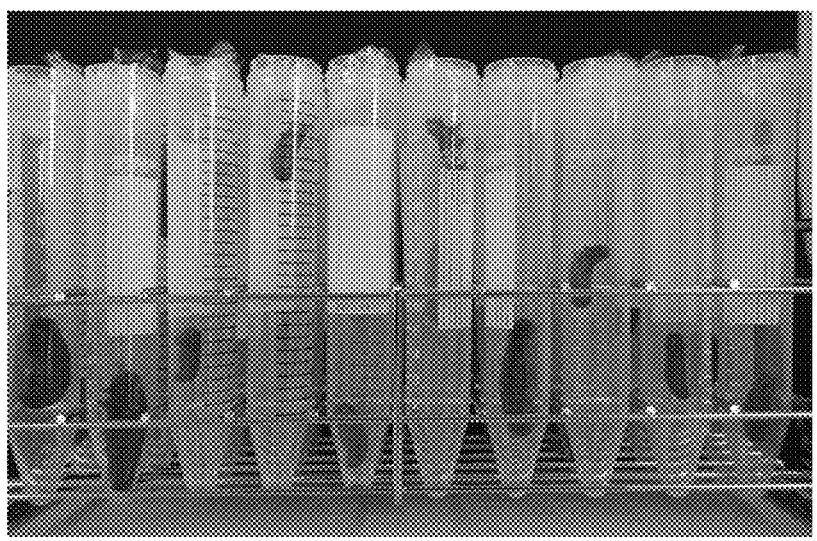
FIGS. 4A to 4C each are a view showing a situation of collecting a bagworm silk thread by using the thread collecting device according to the present invention and a result thereof.
Figure 4:
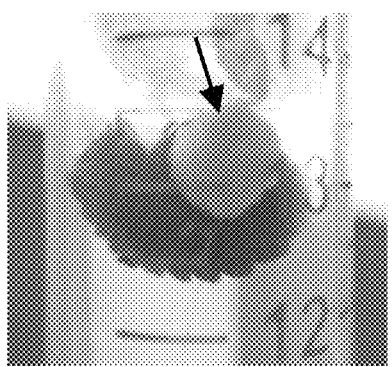
Figure 4:
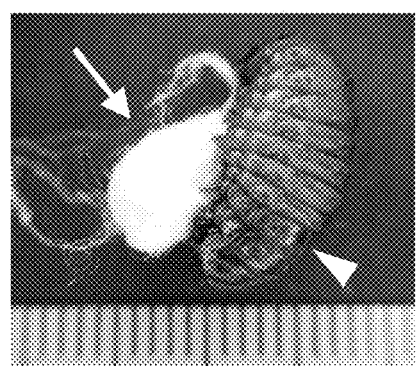

The bagworms were each accommodated in the container of the thread collecting device immediately after taken out of the nest with scissors (FIG. 4A). Subsequently, to prevent the bagworm from getting out, a lid made by rounding Saran Wrap™ (manufactured by Asahi Kasei Corporation) was stuffed as the encapsulating unit into the tube opening. The container was left at 25° C. in this state.

(Result)

As a result, the bagworm in each tube formed a silk thread mass (arrow) after 12 hours as shown in FIG. 4B. FIG. 4C shows a silk thread mass (arrow) and the bagworm (arrowhead) taken out of the tube after 120 hours after accommodation. The silk thread mass, which was pure white and contained no contaminant, made of a pure bagworm silk thread was successfully obtained.

Example 2: Production of Silk Thread Mass by Thread Collecting Device (2)

(Purpose)

A purpose is to verify that use of the thread collecting device with the discharge hole according to the present invention allows for collecting a silk thread mass containing no contaminant from a bagworm in the active stage.

(Method and Result)

Bagworms being used were ten penultimate instar or last instar larvae of *Eumeta minuscula* collected in the field in June. Each individual was in a range of 6.0 mm to 8.0 mm in maximum body width and in a range of 24.0 mm to 30.0 mm in entire length.

A polypropylene pipette tip for 10 mL (manufactured by Eppendorf AG) was used as a container of a verifying thread collecting device. A maximum short axis cross section of an inner space of this container has a width (diameter) of 13.5 mm. Moreover, in a case of using the pipette tip, a pipette connection port corresponds to the container in-and-out hole. Meanwhile, a tube bottommost portion (tip distal portion) was cut to form a 3.5-mm-diameter discharge hole. A 10 mL round-bottomed glass tube (manufactured by AS ONE Corporation) was used as a container of a comparative thread collecting device. Moreover, a test tube rack was used as the holding unit.

Figure 5:
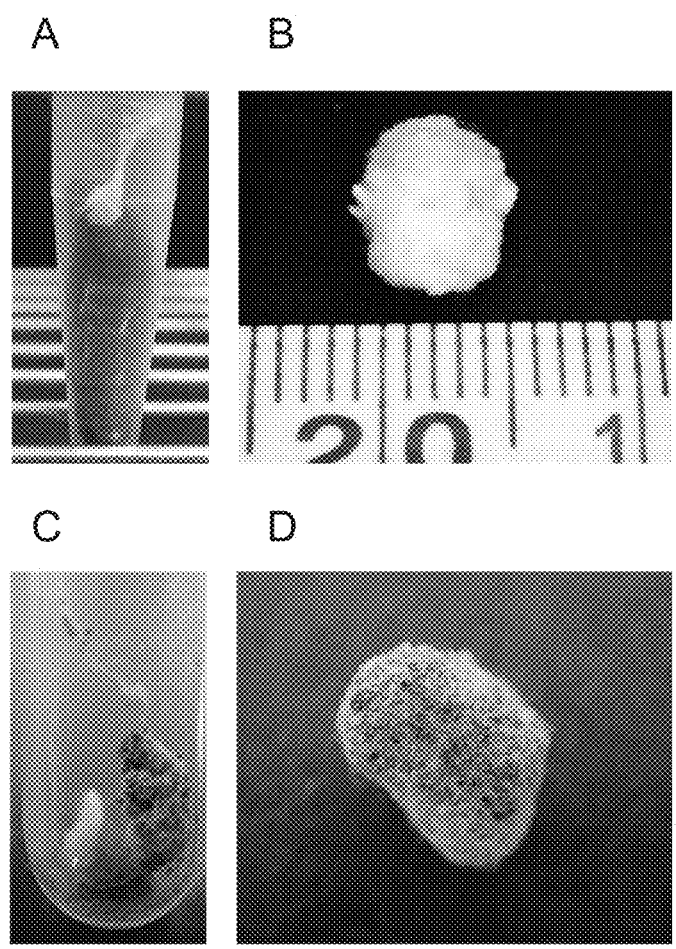
FIGS. 5A to 5D each show a result that demonstrates an effect of a discharge hole of the container of the thread collecting device according to the present invention.

Five of the bagworms were accommodated in each of the containers of the thread collecting devices for verification and for comparison immediately after taken out of the respective nests with scissors. Subsequently, to prevent the bagworms from getting out, the in-and-out hole of each container was closed by covering the opening with a polyethylene film and tightly holding the film with a rubber band. It is to be noted that the container was not sealed, allowing for ventilation inside the container. The container was left at 25° C. for 72 hours in this state. The bagworms excreted excrement in all the containers. However, since the container with the discharge hole for verifying thread collecting device (FIG. 5A) allowed for natural discharge of the excrement out of the container, a silk thread mass, which was pure white and contained no contaminant, made of a pure bagworm silk thread was successfully obtained as in Example 1 as shown in FIG. 5B. In contrast, in the comparative thread collecting device, the excrement remained in the container without being discharged and thus the bagworms frequently tangled the excrement with the spun silk thread as shown in FIG. 5C. As a result, collected silk thread masses were all contaminated by the excrement as shown in FIG. 5D. Accordingly, it has been suggested that use of the container with the discharge hole is preferable in a case of using a bagworm in the active stage in the thread collecting device according to the present invention. Moreover, it has been found that use of the silk thread device according to the present invention allows for easily and simply producing and collecting a silk thread mass made of a pure bagworm silk thread irrespective of a type of the bagworm.

Example 3: Relationship Between Inner Diameter of Container of Thread Collecting Device and Formation of Silk Thread Mass (Purpose)

A purpose is to examine a relationship between a ratio of the width of the maximum short axis cross section of the container inner space of the thread collecting device to the maximum body width of the bagworm accommodated therein and formation of a silk thread mass.
(Method)

A bagworm being used was a last instar larva of *Eumeta minuscula* having an entire length of 30 mm and a maximum body width of 7 mm collected in the field in June.

The width (diameter) of the maximum short axis cross section of the container inner space of the thread collecting device was 9 mm (a polypropylene pipette tip for 2.5 mL, 9 mm in diameter×115 mm in height: Eppendolf AG), 12.0 mm (a 6 mL glass test tube, 12 mm in diameter×75 mm in height: AS ONE Corporation), 15.0 mm (a 15 mL glass test tube, 15 mm in diameter×85 mm in height: AS ONE Corporation), 22.0 mm (a 50 mL glass test tube, 22 mm in diameter×200 mm in height: AS ONE Corporation), 30.0 mm (a 50 mL polypropylene conical tube, 30 mm in diameter×118 mm in height: AS ONE Corporation), and 120 mm (a cylindrical plastic container with a polyethylene lid), 120 mm in diameter×60 mm in height).

A base thread collecting method was conformable to Examples 1 and 2.
(Result)

Figure 6:
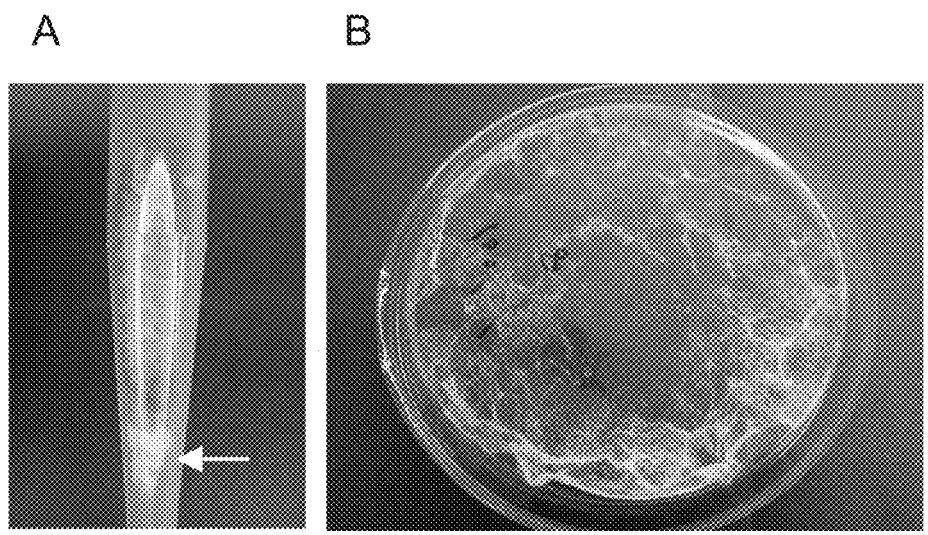
FIGS. 6A and 6B each are a view showing the width of the maximum short axis cross section in the inner space of the container of the thread collecting device according to the present invention and a formation result of a silk thread mass.

In a case of the maximum short axis cross section of the container inner space having a width of 9 mm to 15 mm for the bagworm with the maximum body width of 7 mm, the bagworm formed the silk thread mass in the container (FIG. 6A). However, at a width of the maximum short axis cross section of 22.0 mm or more, that is, more than three times as large as the maximum body width, the bagworm began actively spinning a thread even onto a container inner wall possibly due to an increase in a degree of freedom inside the container. For this reason, a formation rate of a silk thread mass was considerably lowered (not shown). Furthermore, at a width of the maximum short axis cross section of 120 mmn, the bagworm formed no silk thread mass but randomly spun a thread, making a bagworm silk thread stick to the container inner wall (FIG. 6B). This result revealed that the width of the maximum short axis cross section of the container inner space is suitably in a range from 1.2 times or more to less than 3.1 times, preferably from 1.3 times or more to 2.5 times or less, as large as the maximum body width of the bagworm, since the width of the maximum short axis cross section of the container inner space excessively larger than the maximum body width of the bagworm causes a failure in forming a silk thread mass.

Example 4: Relationship Between Inclination of Container of Thread Collecting Device and Formation of Silk Thread Mass (Purpose)

A purpose is to examine a relationship between an inclination of the container of the thread collecting device and the inner space thereof and formation of a silk thread mass.
(Method)

Bagworms being used were last instar larvae of *Eumeta minuscula* collected in the field in June. Each individual was approximately 24 mm in maximum body width and approximately 7 mm in entire length.

Figure 7:
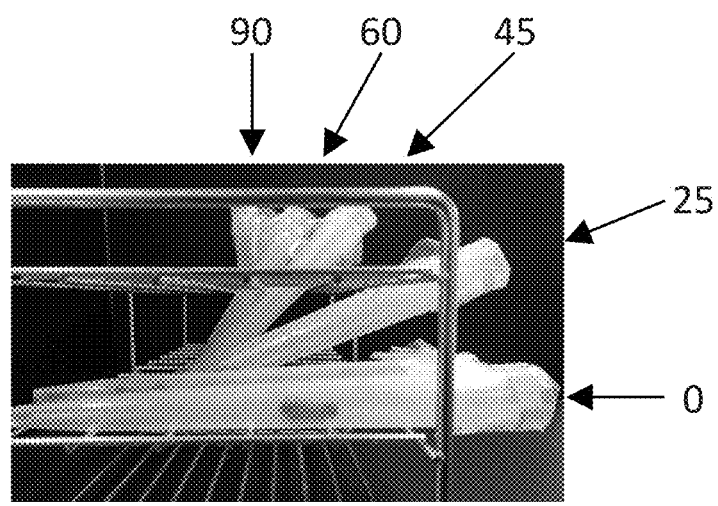
FIG. 7 is a view showing an inclination experiment of the container of the thread collecting device according to the present invention. In the figure, numerical values each represent an inclination angle of the container.

A polypropylene pipette tip for 10 mL (Eppendorf AG) was used as the container of the thread collecting device as in Example 1. A bottommost portion of each tube was provided with a hole with a diameter of 3.5 mm as a discharge hole. Ten tubes were placed on a test tube rack at respective five inclination angles (0 degrees, 25 degrees, 45 degrees, 60 degrees, and 90 degrees) relative to a horizontal plane for every two of the tubes (FIG. 7).

A base thread collecting method was conformable to Examples 1 and 2. Regarding the encapsulating unit, immediately after the bagworm was loaded in the container, the in-and-out hole, that is, the tube opening, was covered with a polyethylene film and the film was tightly held with a rubber band, thereby providing the encapsulating unit. After loaded, the bagworms were observed for three days under the conditions for action.
(Result)

As a result, the bagworms formed substantially spherical silk thread masses inside the tubes with all the inclination angles. This result revealed that in a case of forming a silk thread mass of a bagworm in the thread collecting device according to the present invention, the inclination angle of the container has no substantial influence.

All the publications, patents, and patent applications referred to herein are incorporated herein in their entirety by reference.

The invention claimed is:

1. A device that collects a silk thread(s) from a bagworm(s), the device comprising:
   a container that accommodates the bagworm; and
   an in-and-out hole through which the bagworm is put in and taken out of the container, wherein
- a width of a maximum short axis cross section of an inner space of the container is
  - in a range from 10.8 mm to 27.5 mm if a maximum body width of a last instar bagworm about to be accommodated in the container is in a range from 9.0 mm to 11.0 mm, or
  - in a range from 8.4 mm to 21.3 mm if a maximum body width of a last instar bagworm about to be accommodated in the container is in a range from 7.0 mm to 8.5 mm, wherein the maximum body width is a maximum body width among a width of the cross section including the short axis perpendicular to the long axis from a head tip portion to a tail tip portion, wherein
- the container has a discharge hole at a bottommost portion, and
- the discharge hole has a minimum width longer than a maximum width of excrement of the bagworm being accommodated and a maximum width shorter than a maximum width of a head of the bagworm being accommodated. and wherein the container includes an encapsulating unit configured to encapsulate the bagworm.

2. The device according to claim 1, wherein a long axis of the inner space of the container has an inclination of 60 degrees to 90 degrees relative to a horizontal plane.

3. The device according to claim 1, wherein a shape of the inner space of the container is a tubular shape, a spherical shape, an oval-spherical shape, or a combination thereof.

4. The device according to claim 1, wherein a shape of a short axis cross section of the inner space of the container is a circle, an oval, a polygon, or a combination thereof.

5. The device according to claim 1, wherein an inner wall of the container has a smooth surface.

6. The device according to claim 1, wherein a material of an inside of the container includes an artificial material.

7. A method of collecting a silk thread(s) from a bagworm, the method comprising:
- accommodating a live bagworm having no nest in the container of the device according to claim 1;
- wherein the live bagworm spins a silk thread in the container; and
- collecting the silk thread from the container.

8. The method according to claim 7, further comprising:
- encapsulating the bagworm in the container by closing the in-and-out hole after the accommodating and before the spinning; and
- canceling the encapsulating by opening the in-and-out hole after the spinning and before the collecting.

9. The method according to claim 7, wherein the bagworm is in a last instar.

10. A producing method of producing a silk thread mass of a bagworm, the method comprising:
- accommodating a live bagworm having no nest in the container of the device according to claim 1;
- spinning a silk thread(s) by the bagworm in the container to produce the silk thread mass; and
- collecting the silk thread mass from the container.

11. The producing method according to claim 10, further comprising:
- encapsulating the bagworm in the container by closing the in-and-out hole after the accommodating and before the spinning; and
- canceling the encapsulating by opening the in-and-out hole after the spinning and before the collecting.

12. The producing method according to claim 10, wherein the bagworm is in a last instar.

* * * * *